US00PP12845P2

(12) United States Plant Patent
Segers

(10) Patent No.: US PP12,845 P2
(45) Date of Patent: Aug. 13, 2002

(54) HYBRID TEA ROSE PLANT NAMED 'PREDEMERA'

(75) Inventor: Theodorus A. Segers, Hoofddorp (NL)

(73) Assignee: Florence Creations B.V., Naardwijk (NL)

( * ) Notice: Subject to any disclaimer, the term of this patent is extended or adjusted under 35 U.S.C. 154(b) by 0 days.

(21) Appl. No.: 09/324,085

(22) Filed: Jun. 1, 1999

(51) Int. Cl.[7] ..... A01H 5/00
(52) U.S. Cl. ..... Plt./130
(58) Field of Search ..... Plt./130, 133, 134

(56) References Cited

U.S. PATENT DOCUMENTS

PP11,184 P * 1/2000 Delbard ..... Plt./133
PP11,272 P * 3/2000 Segers ..... Plt./134

OTHER PUBLICATIONS

Copy of QZ PBR 970618, filed May 27, 1997; and EU 4874, granted Sep. 20, 1999.*

UPOV–ROM, 2000/06, Plant Variety Database, GTI Jouve Retrieval Software, citation for 'Predemera'.*

* cited by examiner

*Primary Examiner*—Howard J. Locker
(74) *Attorney, Agent, or Firm*—C. A. Whealy

(57) ABSTRACT

A distinct cultivar of Hybrid Tea rose plant named 'Predemera', characterized by its light greenish ivory-colored flowers that are mostly green on the under side of the petals and mostly ivory on the upper side of the petals; long and strong flowering stems; dark green leaves; good flower production; and excellent postproduction longevity.

1 Drawing Sheet

BACKGROUND OF THE INVENTION

The present invention relates to a new and distinct cultivar of Hybrid Tea Rose plant, botanically known as *Rosa hybrida*, commercially used as a cut flower, and hereinafter referred to by the cultivar name Predemera.

The new cultivar is a product of a planned breeding program conducted by the Inventor in Rijsenhout, The Netherlands. The objective of the breeding program was to develop cut Rose varieties with novel and attractive flower colors, long and strong stems, dark leaves, and good post-production longevity.

The new cultivar originated from a cross made by the Inventor in 1994 of two proprietary selections. The proprietary selection P-151 was the female, or seed, parent and the proprietary selection 93-221 was the male, or pollen, parent. The cultivar Predemera was discovered and selected by the Inventor as a flowering plant within the progeny of the stated cross in a controlled environment in Rijsenhout, The Netherlands. Compared to plants of the parent selections, plants of the new Rose differ in flower color and have a longer postproduction longevity.

Asexual propagation of the new cultivar by cuttings taken at Rijsenhout, The Netherlands, has shown that the unique features of this new Hybrid Tea Rose plant are stable and reproduced true to type in successive generations.

SUMMARY OF THE INVENTION

The following traits have been repeatedly observed and are determined to be the unique characteristics of 'Predemera'. These characteristics in combination distinguish the new Hybrid Tea rose as a new and distinct cultivar:

1. Light greenish and ivory-colored flowers that are mostly green on the under side of the petals and mostly ivory on the upper side of the petals.

2. Long and strong flowering stems.
3. Dark green leaves.
4. Good flower production.
5. Excellent postproduction longevity.

The new Hybrid Tea Rose plant can be compared to the commerical Hybrid Tea Rose cultivars Prebian, not patented, and Pretaner, disclosed in U.S. Plant Pat. No. 11,272. However, in side-by-side comparisons conducted in Rijsenhout, The Netherlands, plants of the cultivar differed from plants of the cultivars Prebian and Pretaner in the following characteristics:

1. Plants of the new Hybrid Tea Rose produce about 10 percent fewer flowering stems per square meter than plants of the cultivars Prebian and Pretaner.
2. Plants of the new Hybrid Tea Rose have slightly shorter flowering stem length than plants of the cultivars Prebian and Pretaner.
3. Plants of the new Hybrid Tea Rose have slightly narrower leaves than plants of the cultivars Prebian and Pretaner.
4. Plants of the new Hybrid Tea Rose have obtuse leaflet apices whereas plants of the cultivars Prebian and Pretaner have acute leaflet apices.
5. Flowers of plants of the new Hybrid Tea Rose are light green and ivory in color whereas flowers of plants of the cultivars Prebian and Pretaner are light yellow to white in color.
6. Flowers of plants of the new Hybrid Tea Rose are smaller than flowers of plants of the cultivars Prebian and Pretaner.
7. Flowers of plants of the new Hybrid Tea Rose do not open as fully as flowers of plants of the cultivars Prebian and Pretaner.
8. Flowers of plants of the new Hybrid Tea Rose have fewer petals than flowers of plants of the cultivars Prebian and Pretaner.

9. Plants of the new Hybrid Tea Rose have shorter peduncles than plants of the cultivars Prebian and Pretaner.
10. Plants of the new Hybrid Tea Rose have longer postproduction longevity than plants of the cultivars Prebian and Pretaner.

The new Hybrid Tea Rose plant has not been observed under all possible environmental conditions. The phenotype may vary significantly with variations in environment such as temperature, light or fertility level, without, however, any variance in genotype.

BRIEF DESCRIPTION OF PHOTOGRAPH

The accompanying colored photograph illustrates the new Hybrid Tea Rose plant, showing the colors as true as it is reasonably possible to obtain in colored reproductions of this type. Colors in the photograph may differ slightly from the color values cited in the detailed botanical description which accurately describe the actual colors of the new Hybrid tea rose. The photograph comprises a side perspective view of typical flowers and leaves of the new Hybrid Tea Rose grown in Rijsenhout, The Netherlands.

DETAILED BOTANICAL DESCRIPTION

The following observations, measurements, values, and comparisons describe plants grown in Rijsenhout, The Netherlands, under glass with average day temperatures of 19° C. and average night temperatures of 17° C.

In the following description, color references are made to The Royal Horticultural Society Colour Chart except where general terms of ordinary dictionary significance are used.

Classification:

*Botanical.*—*Rosa hybrida* cultivar Predemera.

*Commercial.*—Hybrid Tea Rose used as a cut flower.

Parentage:

*Female, or seed, parent.*—*Rosa hybrida* proprietary selection 93-211, not patented.

*Male, or pollen, parent.*—*Rosa hybrida* proprietary selection P-151, not patented.

Propagation:

*Type.*—Cuttings.

*Time to initiate roots.*—About 15 days with soil temperatures of at 25° C.

*Time to develop roots.*—About 28 days with soil temperatures of 25° C.

*Root description.*—Fine, fibrous and well-branched.

Plant description:

*Form.*—Upright; narrow; bushy.

*Growth habit.*—Moderately vigorous.

*Plant height.*—About 100 cm.

*Plant width.*—About 40 cm.

*Productivity.*—About 180 stems per square meter per year under greenhouse year-round production.

*Flowering stems.*—Quantity: Moderate branching; typically three per plant. Length: About 85 cm. Diameter: About 3 cm. Internode length: About 7 cm. Texture: Smooth. Color: 137C. Prickle length: About 8 mm. Prickle color: At the base, 199D; mid-section and towards the apex, 200D.

*Foliage description.*—Leaves arranged alternately, compound with five to seven leaflets per leaf, and generally symmetrical. About 12 compound leaves per flowering stem; typically the distal four leaves have five leaflets and the proximal eight leaves have seven leaflets. Stipules minute; acute; similar in color to leaves; insignificant. Length, seven-leaflet leaves: About 17.5 cm. Width, seven-leaflet leaves: About 13 cm. Length, terminal leaflet of seven-leaflet leaf: About 8.9 cm. Width, terminal leaflet of seven-leaflet leaf: About 5.8 cm. Length, terminal leaflet of five-leaflet leaf: About 8 cm. Width, terminal leaflet of five-leaflet leaf: About 5.5 cm. Leaflet shape: Ovate. Leaflet apex: Obtuse. Leaflet base: Obtuse. Leaflet margin: Serrate. Leaflet texture: Leathery, glabrous, shin. y. Color: Young foliage, upper side: 147A. Young foliage, under side: 200C. Mature foliage, upper side: 139A. Mature foliage, under side: 146A. Venation, upper side: 139A. Venation, under side: 148A. Petiole length: About 3 cm. Petiole diameter: About 2 mm. Petiole color: 147B.

Flower description:

*Flower type and habit.*—Light greenish ivory-colored flowers that are mostly green on the under side of the petals and mostly ivory on the upper side of the petals. Consistently symmetrical rosette flowers. Freely and continuous flowering. Flowers borne singly at terminal apices or in clusters of two. Flowers persistent.

*Flowering season.*—Year-round under greenhouse conditions.

*Fragrance.*—Not detected.

*Flower diameter.*—About 10 cm.

*Flower depth* (*height*).—About 6 cm.

*Flower longevity on plant.*—About 25 days.

*Flower longevity as a cut flower.*—About 20 days.

*Flower buds.*—Shape: Ovate. Length: About 5.6 cm. Diameter: About 3.8 cm. Color: 145A.

*Petals.*—Quantity: About 31 per flower. Typically about four rows with seven or eight petals each. Length: About 5.2 cm. Width: About 7.3 cm. Shape: Orbicular with obtuse apex. Aspect: Petals reflex as the flowers open. Margin: Undulate and entire. Texture: Satiny and slightly rippled. Color: Upper side, when opening: Towards apex, 145A; towards base, 157A. Under side, when opening: Towards apex, 146C; towards base, 145D. Upper side, fully opened: Predominately ivory; at margin, 145B; mid-section and towards base, 157B. Under side, fully opened: Predominantly green; towards apex, 145A; towards base, 145D. Fading to: 157A.

*Sepals.*—Quantity: Typically five per flower. Calyx length: About 4.4 cm. Calyx diameter: About 4.4 cm. Shape: Roughly subulate to acute; apex, sharply acuminate; with three to five lateral extensions. Texture: Smooth. Color: Upper side: 138B, dull. Under side: 146B, dull.

*Peduncles.*—Strength: Strong. Aspect: Erect. Length: About 6.1 cm. Texture: Glabrous. Color: 138A.

*Reproductive organs.*—Stamens: Quantity: About 82 per flower. Anther length: About 3.5 mm. Anther width: About 9 mm. Anther shape: Oblong. Anther color: 17A. Pollen amount: Moderate. Pollen color: 10C. Pistils: Quantity: About 98 per flower. Pistil length: About 1.1 cm. Style length: About 8 mm. Style color: 155B. Stigma color: 22A. Ovary color: 155A.

*Seed.*—Yield: Low. Length: About 8 mm. Diameter: About 5 mm. Color: 159B.

Disease resistance: Moderate resistance to Powdery Mildew has been observed under commercial greenhouse production conditions.

It is claimed:

1. A new and distinct Hybrid Tea Rose plant named 'Predemera', as illustrated and described.

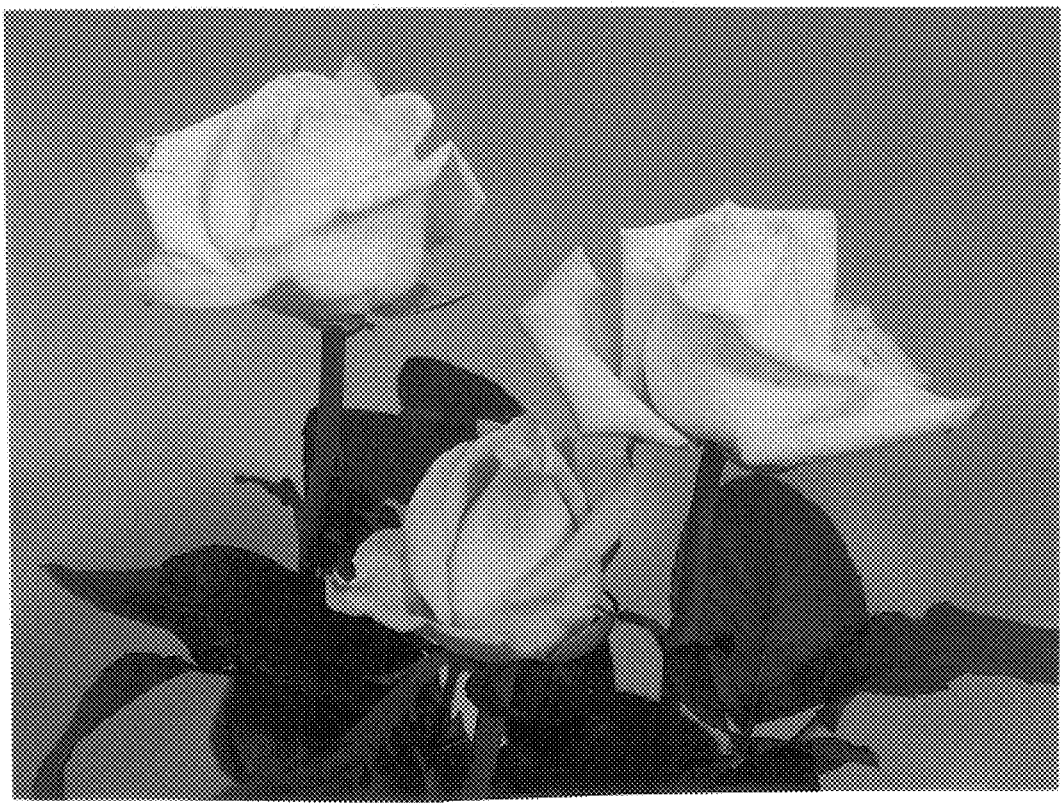

* * * * *